United States Patent [19]

Bohandy et al.

[11] Patent Number: 5,059,891
[45] Date of Patent: Oct. 22, 1991

[54] MICROWAVE METHOD FOR DETECTION OF WEAK LINKS IN SUPERCONDUCTORS

[75] Inventors: Joseph Bohandy, Columbia; Boris F. Kim, Pasadena; Terry E. Phillips, Ellicott City; Frank J. Adrian, Olney; Kishin Moorjani, Silver Spring, all of Md.

[73] Assignee: The Johns Hopkins University, Baltimore, Md.

[21] Appl. No.: 458,066

[22] Filed: Dec. 28, 1989

Related U.S. Application Data

[63] Continuation-in-part of Ser. No. 325,823, Mar. 20, 1989, Pat. No. 4,904,929.

[51] Int. Cl.[5] .................... G01N 27/14; G01R 27/04
[52] U.S. Cl. .................................. 324/71.6; 324/636; 324/629; 505/843

[58] Field of Search ............... 324/71.6, 629, 636, 324/637, 639, 642, 691, 693, 316, 233; 505/842, 843, 845, 847, 700, 701, 726, 727

[56] References Cited

U.S. PATENT DOCUMENTS 4,851,762  7/1989  Kim et al. .......................... 324/71.6
4,904,929  2/1990  Bohandy et al. .................. 324/71.6

Primary Examiner—Jack B. Harvey
Attorney, Agent, or Firm—Robert E. Archibald; Mary Louise Beall

[57] ABSTRACT

Weak links in superconductors are detected by observing the effect of magnetic field modulation on the microwave resistance of superconductors. The phase detected response to the magnetic modulation can show a peak at $T_c$. The presence of peak(s) at temperatures below $T_c$ indicates the presence of weak links in the superconductor.

24 Claims, 3 Drawing Sheets

TUNNELLING JUNCTION i = CURRENT
SC = SUPERCONDUCTOR
NSC = NON-SUPERCONDUCTOR

CONSTRICTION

POINT CONTACT    FIG.1C

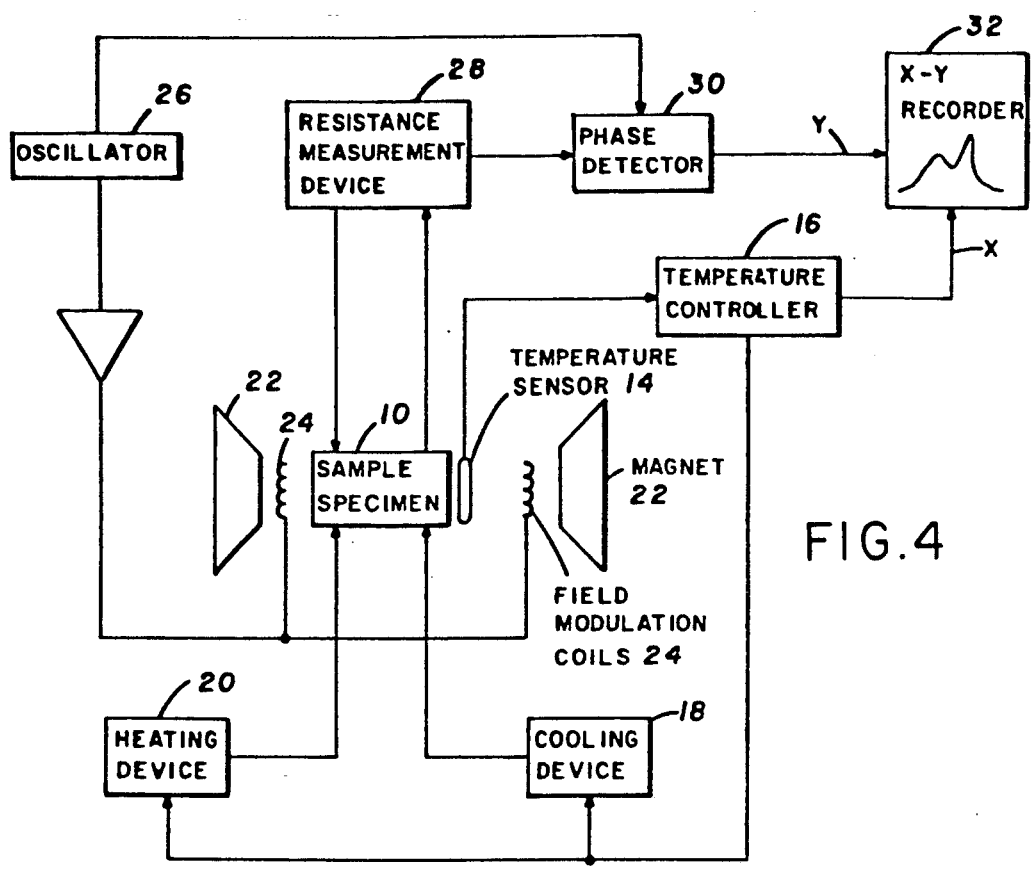
FIG.4
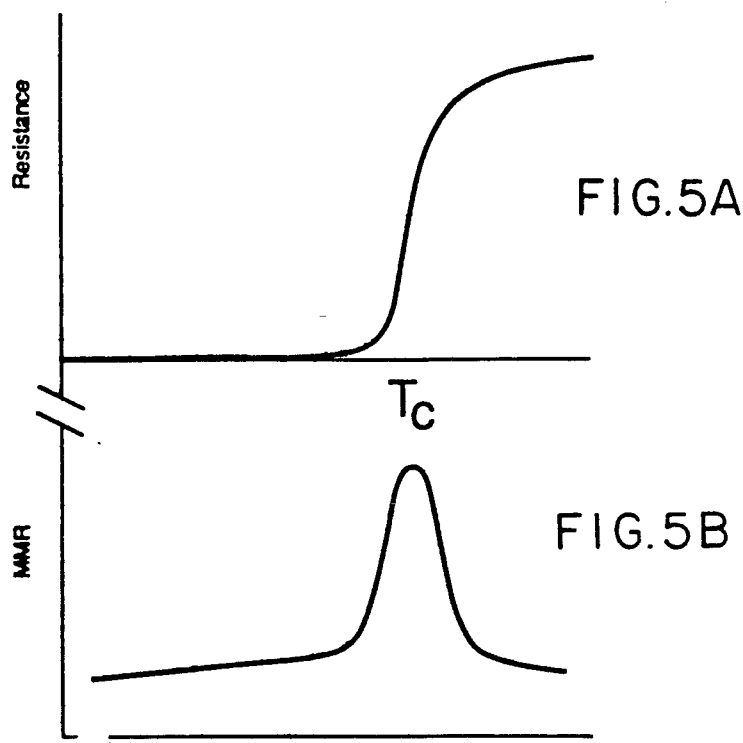
FIG.5A
FIG.5B

MICROWAVE METHOD FOR DETECTION OF WEAK LINKS IN SUPERCONDUCTORS

STATEMENT OF GOVERNMENTAL INTEREST

The Government has rights in this invention pursuant to Contract No. N00039-87-C-5301 awarded by the Department of the Navy.

BACKGROUND OF THE INVENTION

This is a continuation-in-part of U.S. patent application Ser. No. 325,823, now U.S. Pat. No. 4,904,929 filed Mar. 20, 1989 and entitled "Method for Detection of Weak Links in the Current Path of Electrically Continuous Superconductors."

The present invention relates to a method for detecting the existence of weak links in superconducting samples; they need not be electrically continuous. The apparatus used in the method of this invention is generally described in commonly assigned U.S. Pat. No. 4,851,762 entitled "Novel Technique Using Magnetic Field Dependent Phase Detection for Detection of Superconductivity" filed Sept. 31, 1988 and incorporated herein by reference. The method of this invention is related to the method of this patent in which the magnetically modulated resistance response of the sample is phase detected and recorded as a function of temperature.

OBJECTS OF THE INVENTION

It is an object of the present invention to provide a method for the rapid and accurate detection of the presence of weak links in superconducting samples.

It is also an object of the present invention to determine the presence or absence of weak links by measuring the magnetically modulated microwave resistance of a sample while varying the temperature and maintaining the magnetic field below its critical value.

It is another object of the invention to provide a method to study the performance of superconductors containing weak links in response to the action of an applied magnetic field while varying the temperature.

It is also an object of the present invention to provide a method to study the behavior of superconductors containing weak links in response to changes in the magnetic field.

It is also an object of the present invention to provide a method to study the behavior of superconductors containing weak links in response to changes in applied current.

Still another object of the present invention is to provide a quality control method for the fabrication of superconducting thin films.

SUMMARY OF THE INVENTION

The present invention relates to a method to detect the presence of weak links in superconducting samples by measuring the magnetically modulated resistance (MMR) of the sample. The particular technique used is a magnetically modulated microwave absorption or MAMMA technique. The MMR technique used in U.S. Pat. No. 4,904,939 (the parent application) is called a magnetically modulated electrical resistance or MAMER technique.

A weak link is a connection between at least two superconducting regions and has a much lower critical current than the superconductors it connects. It can be penetrated by a magnetic field. FIG. 1 represents three examples of weak links: tunnelling junction, constriction and point contact.

The method of the invention is based on two principles:

1. At temperatures below the superconducting phase transition temperature ($T_c$) the resistance of the sample goes to zero, and 2. The superconductive phase transition temperature is magnetic field dependent.

The first principle is demonstrated graphically by FIG. 2 representing the amount of resistance in a sample in relation to temperature. The graph shows a precipitous drop in resistance at $T_c$.

According to the second principle, the application of a magnetic field at a strength below its critical value causes $T_c$ to drop to a lower value. This is graphically represented in FIG. 3 wherein an increase in magnetic field causes the $T_c$ to shift from point A to point B.

The invention combines both of these principles in a method to determine accurately and rapidly whether a particular specimen contains weak links.

According to the invention, the resistance of the sample is determined while slowly changing the temperature and also while modulating an applied magnetic field at a defined frequency. The magnetic field is maintained below its critical value which is defined as the maximum magnetic field the superconductive state can be subjected to at a temperature below To and still remain superconductive. The critical value for the magnetic field of weak links is less than for the bulk superconductor. This allows a series of tests to be performed, each measuring the resistance of the sample after each temperature change but at different applied magnetic fields. The results can be compared and provide a method to study the behavior of weak links in superconductive samples in response to the application of different magnetic fields. The invention also provides a way to study the behavior of weak links in response to the application of different currents.

The modulation of the magnetic field must be such that the total field applied to the sample is always of the same polarity. In other words, the total field does not change direction. The temperature may be swept from high values to low values or vice versa.

The apparatus used in the method of this invention is generally described in U.S. Pat. No. 4,851,762. The particular apparatus is represented in FIG. 4.

The method of the present invention is related to the method of U.S. Pat. No. 4,851,762 in which the magnetically modulated resistance (MMR) response of the sample is phase detected and recorded as a function of temperature. Unlike the method of parent U.S. Pat. No. 4,904,939 which measures the magnetically modulated electrical resistance (MAMER), this invention measures the microwave resistance of the sample as a function of temperature and in the presence of a modulated magnetic field. It is called the MAMMA technique for magnetically modulated microwave absorption. The sample need not be electrically continuous.

The temperature is sequentially changed in equal increments, producing first signals at each temperature change. The microwave resistance is determined at each temperature change, producing second signals. Each second signal is compared to the modulation frequency by phase detection, producing third signals. A series of coordinate points is plotted on an x-y recorder, wherein one axis represents the first signals and the other axis represents the third signals.

Because the resistance of the sample is magnetic field dependent and the field is modulated at a particular frequency, when the resistance is phase detected at that same frequency, its derivative with respect to field as a function of temperature is the response actually recorded on x-y recorder 32. For superconducting materials not containing weak links, U.S. Pat. No. 4,851,762 teaches that, at $T_c$, this response is also proportional to the derivative of the resistance with respect to temperature. This relationship is demonstrated in FIG. 5 wherein 5a shows the unmodulated resistance vs. temperature measurement for a conventional superconductor and 5b demonstrates the response obtained by the magnetically modulated response (MMR) of the present invention. As shown in 5b, the MMR for this conventional superconductor is a very well defined peak at $T_c$ which corresponds to the derivative of the resistance curve of 5a. Additional peak(s) at temperatures below $T_c$ indicate(s) the existence of weak links. The size and shape of the additional peaks vary: some are quite broad and some may be in the opposite direction from that shown in FIG. 5b.

The superconducting sample to be used in the present invention may be thin film or bulk, either of which can be non-granular or granular; it need not be electrically continuous.

The static magnetic field is in the range of 1 Gauss to 5 kilogauss and is modulated at a frequency in the range of 1 to 100 kilohertz. The applied magnetic field modulation is in the range of 0.1 to 5 Gauss but must be less than that of the static field. The microwave power imposed on the sample is in the range of 0.01 to 200 milliwatts.

The temperature is recorded and the resistance is determined only at preselected temperature increments in a linear temperature progression. The temperature range is determined experimentally and depends on the nature of the sample being tested.

BRIEF DESCRIPTION OF THE DRAWINGS

FIGS. 1a, 1b and 1c are representations of several types of weak links.

FIG. 4 is a block diagram of the apparatus used in the present invention.

FIGS. 5a and 5b represent the unmodulated resistance measurement and the MMR measurement for a conventional superconductor.

DESCRIPTION OF THE PREFERRED EMBODIMENT

Figure 1A:
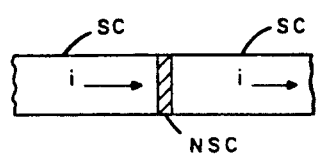
Figure 1B:
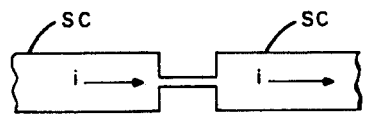
Figure 2:
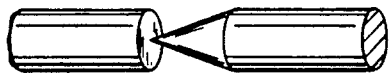
FIG. 2 is a graphic representation of the precipitous drop in resistance demonstrated by a superconductor at $T_c$.
Figure 2:
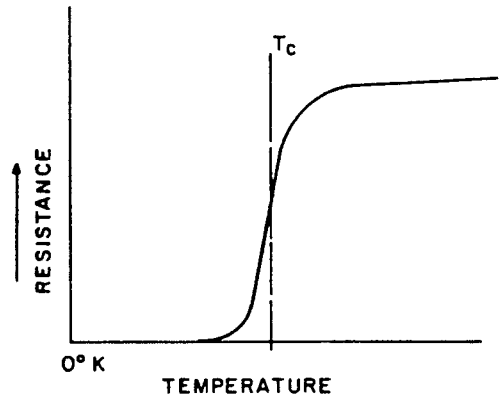
Figure 3:
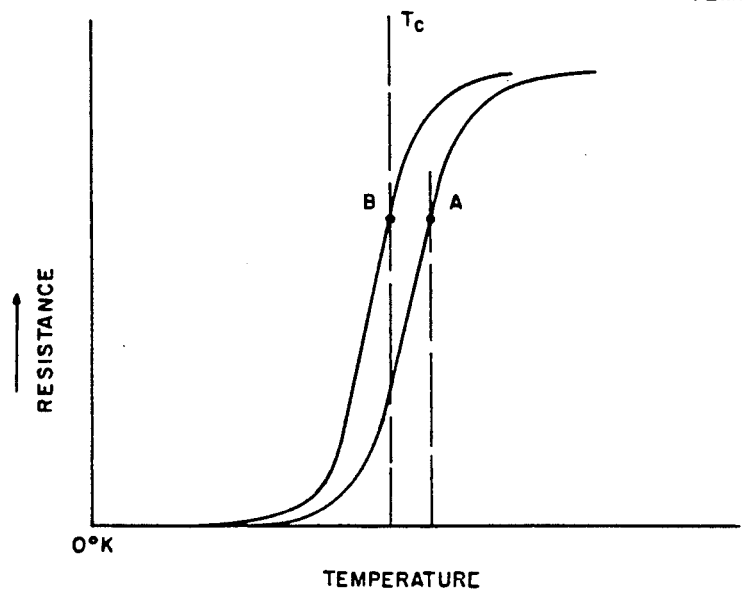
FIG. 3 is a graphic representation of the magnetic field dependence of the superconductor $T_c$.

The preferred embodiment shown in FIG. 4 uses a resonant microwave cavity and a microwave bridge (not shown) as the resistance measuring device 28. This apparatus is described in U.S. Pat. No. 4,851,762, incorporated herein by reference. A superconducting sample 10 is placed within the cavity and subjected to microwave power of 2 milliwatts provided by the microwave bridge. The bridge is equipped with a microwave detector to detect microwave power reflected from the cavity. Measuring the microwave power is an indirect method of measuring the microwave resistance of the sample.

The temperature sensor 14 is connected to a temperature controller 16 controlling the temperature of the sample through the action of cooling device 18 and heating device 20.

A constant dc magnetic field of 30 G is applied to a Bi-Sr-Ca-Cu-O (BSCCO) superconducting thin film sample 10 by magnet 22. This field is modulated at 10 KHz by the application of a 5 G ac magnetic field supplied by oscillator 26 through field modulation coils 24. At all times the total magnetic field is of the same polarity and below the critical value for the superconductor.

The voltage output from the microwave detector is compared, in phase detector 30, to the signal from oscillator 26. As the temperature is changed or swept, changes in resistance are phase detected by phase detector 30 at the modulation frequency supplied by oscillator 26. Computer signals "y" from phase detector 30 and related computer signals "x" from temperature controller 16 form coordinate points on x-y recorder 32.

Figure 6:
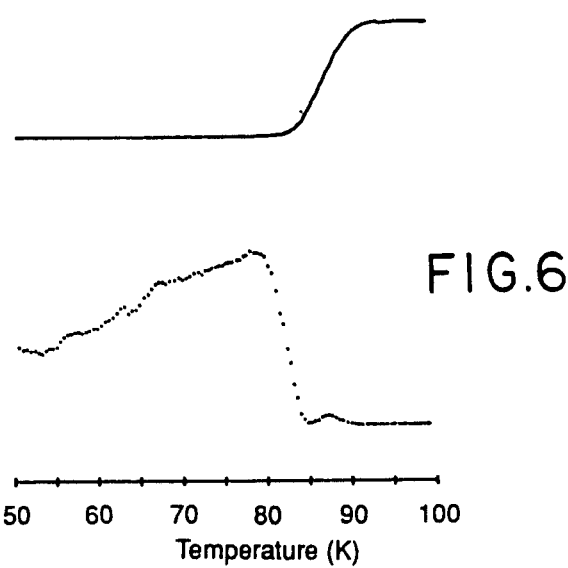
FIG. 6 is a MAMMA spectrum based on a microwave resistance measurement (dotted line) and its simultaneously recorded unmodulated microwave resistance curve (solid line).

The MAMMA response on the x-y recorder is reproduced in FIG. 6 and shows, in a dotted line formed by the coordinate points, a small peak at $T_c$ (approximately 87° K). The solid line is the corresponding simultaneously recorded unmodulated microwave resistance curve demonstrating the precipitous drop in resistance at $T_c$. A second broad peak is also presented at a temperature lower than $T_c$, demonstrating the presence of weak links in the sample.

DISCUSSION

In practice, the MAMMA method is operated as described above. An appropriate magnetic field is imposed on the superconducting sample and the magnetic field is modulated in such a fashion that the total magnetic field always has the same polarity. The temperature of the sample is slowly changed and the phase detected resistance of the sample is recorded at each temperature change. The $T_c$ can be identified by the appearance of a peak corresponding to a sharp or precipitous drop in resistance shown on the simultaneously recorded unmodulated microwave resistance curve, indicating a precipitous drop in resistance. If a peak does appear at temperatures below $T_c$, the superconducting sample contains weak links. The number of weak links increases with the granularity of the sample. In very granular samples, the inventors have observed that the peak at $T_c$ may not be detectable.

The method of the present invention may be operated several times on the same sample but at different magnetic fields. It may also be practiced with the application of different electrical currents. This provides a technique to study the behavior of weak links as a function of magnetic field and/or current.

Figure 7:
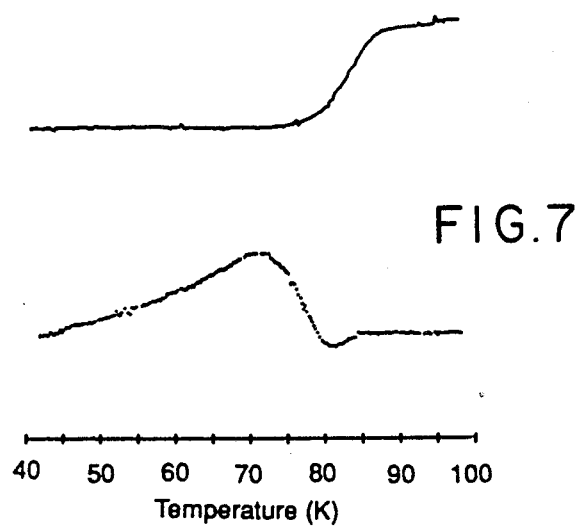
FIG. 7 is a MAMMA spectrum based on a microwave resistance measurement (dotted line) and its simultaneously recorded unmodulated microwave resistance curve (solid line).
Figure 8:
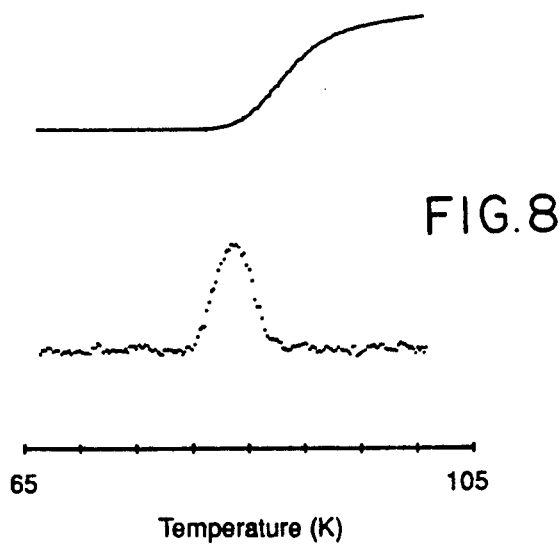
FIG. 8 is a MAMER spectrum based on an electrical resistance measurement (dotted line) and its simultaneously recorded unmodulated dc resistance curve (solid line). Both FIGS. 7 and 8 relate to resistance measurements made on the same superconducting film.

FIGS. 7 and 8 are MMR spectra (dotted line) and their respective simultaneously recorded unmodulated resistance curves (solid line) for the same BSCCO superconducting sample. FIG. 7 is a MAMMA spectrum demonstrating the method of the present continuation-in-part invention and FIG. 8 is a MAMER spectrum demonstrating the method of the parent invention. For both, a static magnetic field of 30 Gauss modulated by the application of a 5 Gauss, 10 kilohertz ac magnetic field, was imposed on the sample. Additionally, the MAMMA demonstration imposed approximately 5 milliwatts of microwave power on the superconducting sample within the cavity. For the MAMER demonstration, 10 microamperes of electrical current were applied the superconducting sample. Both spectra show peaks below $T_c$, which can be approximately determined by the location of the midpoint of the slope of the dc resistance curve. These spectra demonstrate that this particular superconducting sample contains weak links. Also, since no peak at $T_c$ is detectable, it can be inferred that this particular sample is rather granular.

This sample was prepared by laser ablation from a bulk sample of BSCCO.

The MAMMA method has been used to test for weak links in Y-Ba-Cu-O and Bi-Sr-Ca-Cu-O with similar results.

As discussed in U.S. Pat. No. 4,851,762, the MMR method may be used to identify multiple superconducting phases characterized by the presence of different $T_c$'s. Each $T_c$ is identified by a well defined MMR peak produced concomitantly with a precipitous drop in unmodulated resistance for each phase present in the superconducting sample. The presence of a peak not associated with a precipitous drop in resistance and located below any one of the several possible $T_c$'s indicates the presence of weak links in the superconductive sample. A superconducting sample may be multiphasic because it is a mixed sample or because the superconductor itself is multiphasic. An example of the latter is BSCCO having $T_c$'s at approximately 110° K. and 80° K.

Computer means, not shown, facilitate the operation of the process of the invention. Typical software used in the computer means is disclosed in the above referenced patent.

The invention described is not intended to be limited to the embodiments disclosed but includes modifications made within the true spirit and scope of the invention.

What is claimed is:

1. A method for detecting weak links in a superconducting sample comprising:
    a) placing the superconducting sample in a resonant cavity;
    b) imposing a magnetic field in the range of 1 G to 5 KG on the sample;
    c) modulating the imposed magnetic field, in the range 0.1 G–5 G and at a frequency in the range of 1 KHz–100 KHz, in such a fashion that the total magnetic field is always of the same polarity;
    d) sequentially changing the temperature of the sample, recording the temperature at each change and producing first signals;
    e) imposing microwave power in the range of 0.01 milliwatts to 200 milliwatts on the sample, measuring the microwave power reflected from the cavity at each temperature change and producing second signals;
    f) comparing the second signals to the modulation frequency by phase detection and producing third signals;
    g) plotting a series of coordinate points where one axis represents said first signals and the other axis represents said third signals; and
    h) measuring the unmodulated microwave resistance of the sample as a function of temperature to obtain a resistance vs. temperature curve;

wherein the existence of weak links in the superconducting sample is indicated by the presence of at least one peak formed by the series of coordinate points at a temperature lower than the $T_c$ of the superconducting sample where $T_c$ is the superconducting phase transition temperature.

2. A method according to claim 1, wherein the sample is one of a thin film superconductor and a bulk superconductor.

3. A method according to claim 2, wherein the sample is one of a granular superconductor and a non-granular superconductor.

4. A method according to claim 1, wherein the sample is one of electrically continuous and electrically discontinuous.

5. A method according to claim 1, including repeating steps a-14 g at least one time, each repeat of step b imposing a different strength magnetic field with each imposed magnetic field being different in strength from those used previously.

6. A method according to claim 1, including:
    i) applying an electric current to the sample; and repeating steps a–g at least one time, each repeat of step e applying a different strength current with each applied current being different in strength from those used previously.

7. A method according to claim 1, wherein steps g and h occur simultaneously.

8. A method for detecting weak links in a superconducting sample comprising:
    placing the superconducting sample in a resonant cavity;
    imposing a magnetic field of 30 G on the sample;
    modulating the imposed magnetic field at 5 G and at a frequency of 10 KHz, in such a fashion that the total magnetic field is always of the same polarity;
    sequentially changing the temperature of the sample, recording the temperature at each change and producing first signals;
    imposing approximately 5 milliwatts of microwave power on the sample, measuring the microwave power reflected from the cavity at each temperature change and producing second signals;
    comparing the second signals to the modulation frequency by phase detection and producing third signals;
    plotting a series of coordinate points where one axis represents said first signals and the other axis represents said third signals; and
    measuring the unmodulated resistance of the sample as a function of temperature and plotting a resistance vs. temperature curve;

wherein the existence of weak links in the superconducting sample is indicated by the presence of at least one peak formed by the series of coordinate points at a lower temperature than the $T_c$ of the superconducting sample where $T_c$ is the superconducting phase transition temperature.

9. A method for detecting weak links in a superconducting sample comprising:
   a) providing the superconducting sample;
   b) imposing a magnetic field on the sample;
   c) modulating the imposed magnetic field in such a fashion that the total magnetic field is always of the same polarity;
   d) sequentially changing the temperature of the sample, recording the temperature at each change and producing first signals;
   e) measuring the microwave resistance of the sample at each temperature change and producing second signals;
   f) comparing the second signals to the modulation frequency by phase detection and producing third signals; and
   g) plotting a series of coordinate points where one axis represents said first signals and the other axis represents said third signals;
   wherein the microwave resistance in step e is measured by:
   h) placing the sample in a resonant cavity;
   i) imposing microwave power on the sample;
   j) measuring the microwave power reflected from the cavity; and
   k) applying an electric current to the sample,
   l) repeating steps a-g at least one time, each repeat of said step e applying a different strength electric current with each applied electric current being different in strength from those used previously;
   wherein the existence of weak links in the superconducting sample is indicated by the presence of at least one peak formed by the series of coordinate points at a temperature lower than the $T_c$ of the superconducting sample where $T_c$ is the superconducting phase transition temperature.

10. A method according to claim 9, wherein the temperature is recorded and the resistance is measured only at preselected temperature increments in a linear temperature progression.

11. A method according to claim 9, including:
    m) measuring the unmodulated microwave resistance of the sample as a function of temperature and plotting a resistance vs. temperature curve.

12. A method according to claim 11, wherein steps g and m occur simultaneously.

13. A method according to claim 9, wherein said first signal is the temperature and said third signal is the phase detected resistance with respect to the temperature.

14. A method according to claim 9, wherein the sample is one of electrically continuous and electrically discontinuous.

15. A method according to claim 9, wherein the sample is one of a thin film superconductor and a bulk superconductor.

16. A method according to claim 15, wherein the sample is one of a granular superconductor and a non-granular superconductor.

17. A method according to claim 9, including repeating steps a-g at least one time, each repeat of step b imposing a different strength magnetic field with each imposed magnetic field being different in strength from those used previously.

18. A method for detecting weak links in a superconducting sample comprising:
    a) placing the superconducting sample in a resonant cavity;
    b) imposing a magnetic field in the range of 1 G to 5 KG on the sample;
    c) modulating the imposed magnetic field, in the range 0.1 G–5 G and at a frequency in the range of 1 KHz–100 KHz, in such a fashion that the total magnetic field is always of the same polarity;
    d) sequentially changing the temperature of the sample, recording the temperature at each change and producing first signals;
    e) imposing microwave power in the range of 0.01 milliwatts to 200 milliwatts on the sample, measuring the microwave power reflected from the cavity at each temperature change and producing second signals;
    f) comparing the second signals to the modulation frequency by phase detection and producing third signals;
    g) plotting a series of coordinate points where one axis represents said first signals and the other axis represents said third signals;
    h) applying an electric current to the sample; and
    i) repeating steps a-g at least one time, each repeat of step e applying a different strength current with each applied current being different in strength from those used previously;
    wherein the existence of weak links in the superconducting sample is indicated by the presence of at least one peak formed by the series of coordinate points at a temperature lower than the $T_c$ of the superconducting sample where $T_c$ is the superconducting phase transition temperature.

19. A method according to claim 18, including:
    j) measuring the unmodulated microwave resistance of the sample as a function of temperature to obtain a resistance vs. temperature curve.

20. A method according to claim 18, wherein the sample is one of a thin film superconductor and a bulk superconductor.

21. A method according to claim 18, wherein the sample is one of a granular superconductor and a non-granular superconductor.

22. A method according to claim 18, wherein the sample is one of electrically continuous and electrically discontinuous.

23. A method according to claim 18, including repeating steps a-g at least one time, each repeat of step b imposing a different strength magnetic field with each imposed magnetic field being different in strength from those used previously.

24. A method according to claim 18, wherein steps g and j occur simultaneously.

* * * * *

UNITED STATES PATENT AND TRADEMARK OFFICE
CERTIFICATE OF CORRECTION

PATENT NO. : 5,059,891
DATED : October 22, 1991
INVENTOR(S) : Joseph Bohandy, etal.

It is certified that error appears in the above-identified patent and that said Letters Patent is hereby corrected as shown below:

Column 6, line 27, delete "a-14 g" and insert -- a - g --.

Signed and Sealed this

Second Day of March, 1993

Attest:

STEPHEN G. KUNIN

Attesting Officer

Acting Commissioner of Patents and Trademarks